US009186230B2

(12) United States Patent
Casabonne et al.

(10) Patent No.: US 9,186,230 B2
(45) Date of Patent: Nov. 17, 2015

(54) NOZZLE FOR A POLISHER

(75) Inventors: Thierry Casabonne, Bordeaux (FR);
Vianney Jm Ruellan, Bordeaux (FR);
Ulrich Saxer, Forch (CH)

(73) Assignee: SOCIETE POUR LA CONCEPTION DES APPLICATIONS DES TECHNIQUES ELECTRONIQUE, Merignac (FR)

( * ) Notice: Subject to any disclaimer, the term of this patent is extended or adjusted under 35 U.S.C. 154(b) by 0 days.

(21) Appl. No.: 13/808,451

(22) PCT Filed: Jul. 4, 2011

(86) PCT No.: PCT/FR2011/051570
§ 371 (c)(1),
(2), (4) Date: Jun. 18, 2013

(87) PCT Pub. No.: WO2012/004505
PCT Pub. Date: Jan. 12, 2012

(65) Prior Publication Data
US 2013/0266908 A1 Oct. 10, 2013

(30) Foreign Application Priority Data

Jul. 7, 2010 (FR) ...................................... 10 55510

(51) Int. Cl.
*A61C 3/00* (2006.01)
*A61C 17/00* (2006.01)
*A61C 3/025* (2006.01)
*B05B 1/26* (2006.01)

(52) U.S. Cl.
CPC .................. *A61C 17/00* (2013.01); *A61C 3/025* (2013.01); *B05B 1/267* (2013.01)

(58) Field of Classification Search
CPC ....................................................... A61C 3/025
USPC ............................................. 433/88; 451/102
See application file for complete search history.

(56) References Cited

U.S. PATENT DOCUMENTS

| 4,768,709 | A | * | 9/1988 | Yie ..................................... 239/8 |
| 4,776,794 | A | * | 10/1988 | Meller .......................... 433/216 |
| 5,765,759 | A | * | 6/1998 | Bruns et al. .................... 239/398 |
| 6,325,624 | B1 | * | 12/2001 | Kutsch et al. ................... 433/88 |
| 6,837,709 | B2 | * | 1/2005 | Sierro et al. ..................... 433/88 |
| 6,939,205 | B2 | * | 9/2005 | Hopf et al. ....................... 451/38 |
| 8,256,117 | B2 | * | 9/2012 | Hennig ........................ 29/889.7 |
| 8,448,880 | B2 | * | 5/2013 | Hashish et al. ................ 239/434 |
| 2004/0202980 | A1 | * | 10/2004 | Policicchio ..................... 433/88 |
| 2005/0175960 | A1 | * | 8/2005 | Wiek et al. ...................... 433/88 |
| 2006/0252006 | A1 | * | 11/2006 | Apelker et al. .................. 433/88 |
| 2007/0042316 | A1 | * | 2/2007 | Pichat et al. .................... 433/80 |

FOREIGN PATENT DOCUMENTS

JP           2002-165806 A        6/2002

OTHER PUBLICATIONS

International Search Report issued in PCT/FR2011/051570, Sep. 6, 2011.

* cited by examiner

*Primary Examiner* — Ralph Lewis
(74) *Attorney, Agent, or Firm* — Workman Nydegger

(57) ABSTRACT

A polisher nozzle includes a body extending between a proximal portion for connection to a handpiece and a distal portion, the body having a first channel for delivering a polishing powder and a second channel for delivering a fluid. The distal portion includes a chamber disposed in the vicinity of the free end of said distal portion, with the first and second channels opening out into said chamber. The chamber includes two lateral openings each extending in a plane forming an angle with the vertical axial plane of the proximal portion.

10 Claims, 6 Drawing Sheets

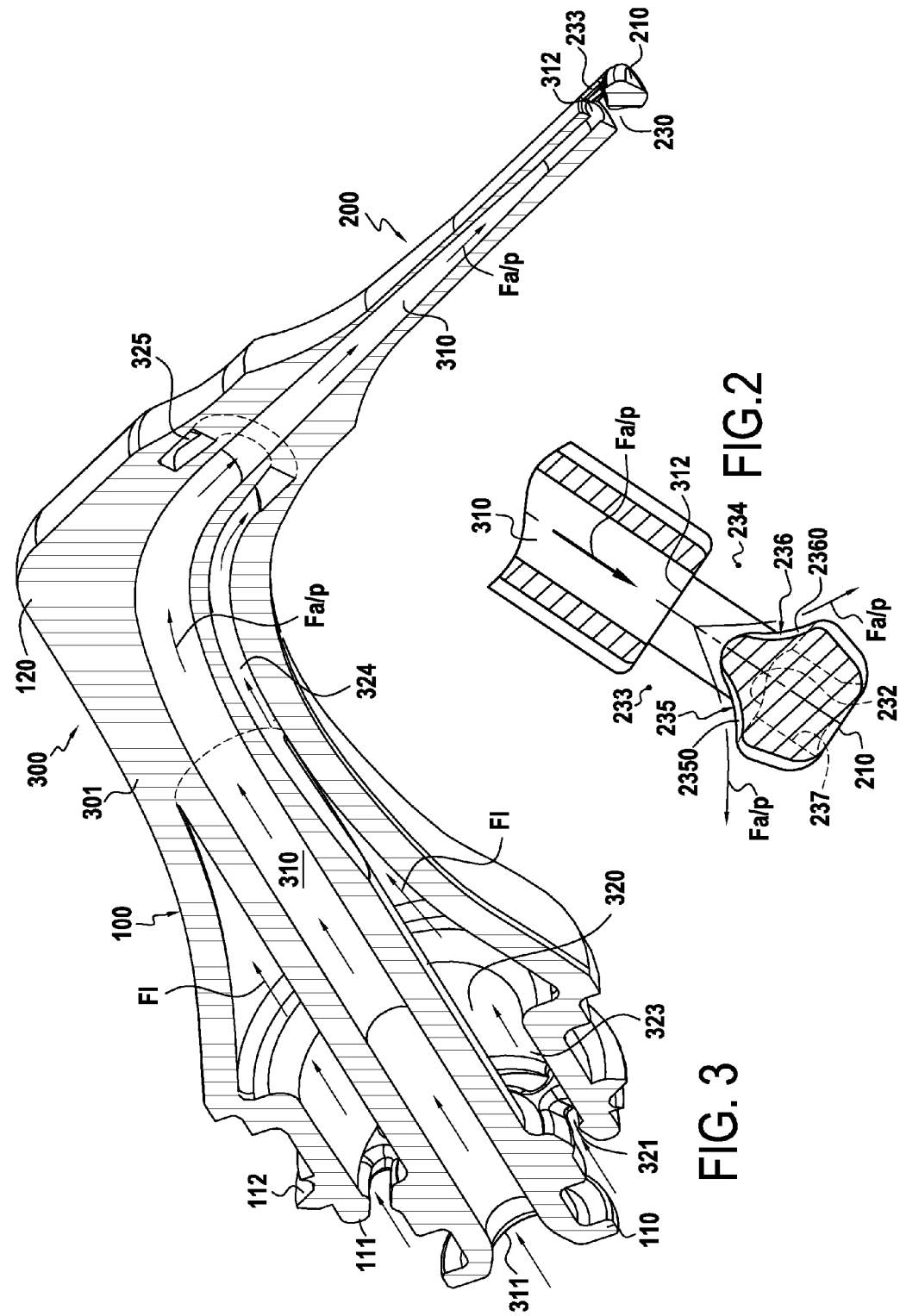

NOZZLE FOR A POLISHER

BACKGROUND OF THE INVENTION

The present invention relates to the field of polishers for delivering simultaneously a fluid such as water and a mixture of air and powder, such polishers being constituted mainly by a handpiece connected to a fluid feed pump and to a compressed air delivery turbine serving to entrain a treatment powder, the handpiece also being provided with an outlet orifice for delivering the fluid and an air and powder mixture.

The invention relates more particularly, but not exclusively, to the polishers used in the field of dentistry for treating periodontal pockets by delivering a fluid and/or an air/powder mixture between the jaw and the tooth in register with the periodontal pocket(s).

The presently available polishers that enable simultaneous delivery of a fluid such as water and a mixture of air and dental powder are fitted with an outlet nozzle that has two distinct ducts, one for delivering the fluid and the other for delivering the air/powder mixture. One such nozzle is described in particular in document US 2007/042316.

In addition, periodontal pockets may be present all around the periphery of a tooth or they may be located at any location around said periphery. Present nozzles do not make it easy to deliver a fluid and an air/powder mixture along the entire periphery of a tooth. With a molar, for example, the practitioner is hindered by the patient's cheek and needs to incline the handpiece of the polisher steeply in order to be able to treat certain portions around a molar. In spite of that, certain pockets can remain inaccessible.

OBJECT AND SUMMARY OF THE INVENTION

An object of the present invention is to propose a novel design of nozzle for a polisher that enables the fluid to be delivered with the air/powder mixture directly from the outlet of the nozzle and that makes it easy to treat the entire periphery of a tooth regardless of its position in the patient's mouth and without it being necessary to incline the handpiece of the polisher too steeply.

This object is achieved with a polisher nozzle comprising a body extending between a proximal portion for connection to a handpiece and a distal portion, said body having a first channel for delivering a polishing powder and a second channel for delivering a fluid, the nozzle being characterized in that said distal portion includes a chamber disposed in the vicinity of the free end of said distal portion, said first and second channels opening out into said chamber, and in that said chamber includes at least one lateral opening extending in a plane forming an angle with the vertical axial plane of said proximal portion.

Thus, the nozzle of the invention directly delivers an outlet spray that is made up simultaneously of a fluid and of an air/powder mixture, the spray being formed in the chamber of the nozzle, i.e. upstream from the outlet proper of the nozzle. The effectiveness of the treatment, e.g. when treating a periodontal pocket, is improved compared with polishers that deliver the fluid and the air/powder mixture via distinct outlets of the nozzle.

In addition, the or each lateral opening of the chamber, i.e. the or each outlet of the nozzle, lies in a respective plane at an angle relative to the vertical plane of the proximal portion of the nozzle for connection to a handpiece. This angle of the or each outlet from the nozzle makes it possible to reach teeth or tooth portions that are usually difficult to reach using prior art nozzles. With the nozzle of the invention, the practitioner may for example treat molars without being hindered by the patient's mouth.

The angle formed between the or each lateral opening and the vertical axial plane of the proximal portion of the nozzle lies in the range 45° to 90° and is preferably situated around 70°.

In an embodiment of the invention, the chamber of the nozzle has two opposite lateral openings, each extending in a plane that forms an angle with the vertical axial plane of said proximal portion, thus enabling a spray to be delivered from each side of the nozzle and thus making it easier to perform the treatment around a tooth.

According to a particular characteristic of the invention, the end wall of the chamber presents an opening that opens out into the free end of the distal portion, said opening being in alignment with the outlet orifice of the second channel into the chamber.

According to another particular characteristic of the invention, the end wall of the chamber includes a deflector arranged facing the outlet orifice from the first channel into the chamber so as to direct the polishing powder delivered by the orifice of the first channel towards the or each lateral opening of the chamber. The polishing powder and some of the fluid reaching the chamber are thus sent towards the zone for treatment while performing turbulent movement.

According to another particular characteristic of the invention, the distal portion presents an elliptical shape having its major axis forming an angle with the vertical axial plane of the proximal portion, the plane of each lateral opening of the chamber being substantially parallel to the major axis of the ellipse. This elliptical shape and its orientation make it easier to insert the end of the nozzle between the jaw and the tooth for treatment and also make it easier to move it around the tooth while limiting any risk of injuring tissue.

The present invention also provides a polisher comprising a handpiece including a first channel for feeding polishing powder and a second channel for feeding fluid, the polisher being characterized in that it further includes a nozzle of the invention, the proximal portion of said nozzle being connected to the handpiece, said first channel for feeding polishing powder co-operating with the first channel in the nozzle, and said second channel for feeding fluid co-operating with the second channel in the nozzle.

According to a particular characteristic of the polisher of the invention, the polisher includes an interchangeable powder tank.

According to another characteristic of the polisher of the invention, the first powder feed channel includes a powder-taking opening that is present in the tank, the tank having a piston that is suitable for closing said powder-taking opening in order to stop powder delivered by the nozzle.

BRIEF DESCRIPTION OF THE DRAWINGS

Other characteristics and advantages of the invention appear from the following description of particular embodiments of the invention, given as non-limiting examples and with reference to the accompanying drawings, in which:

FIG. 2 is a section view of the end of the FIG. 1 nozzle on a plane II-II;

FIGS. 3 and 4 are views in perspective and in section respectively on planes III-III and IV-IV of the nozzle of FIG. 6;

DETAILED DESCRIPTION OF THE EMBODIMENTS OF THE INVENTION

Figure 1:
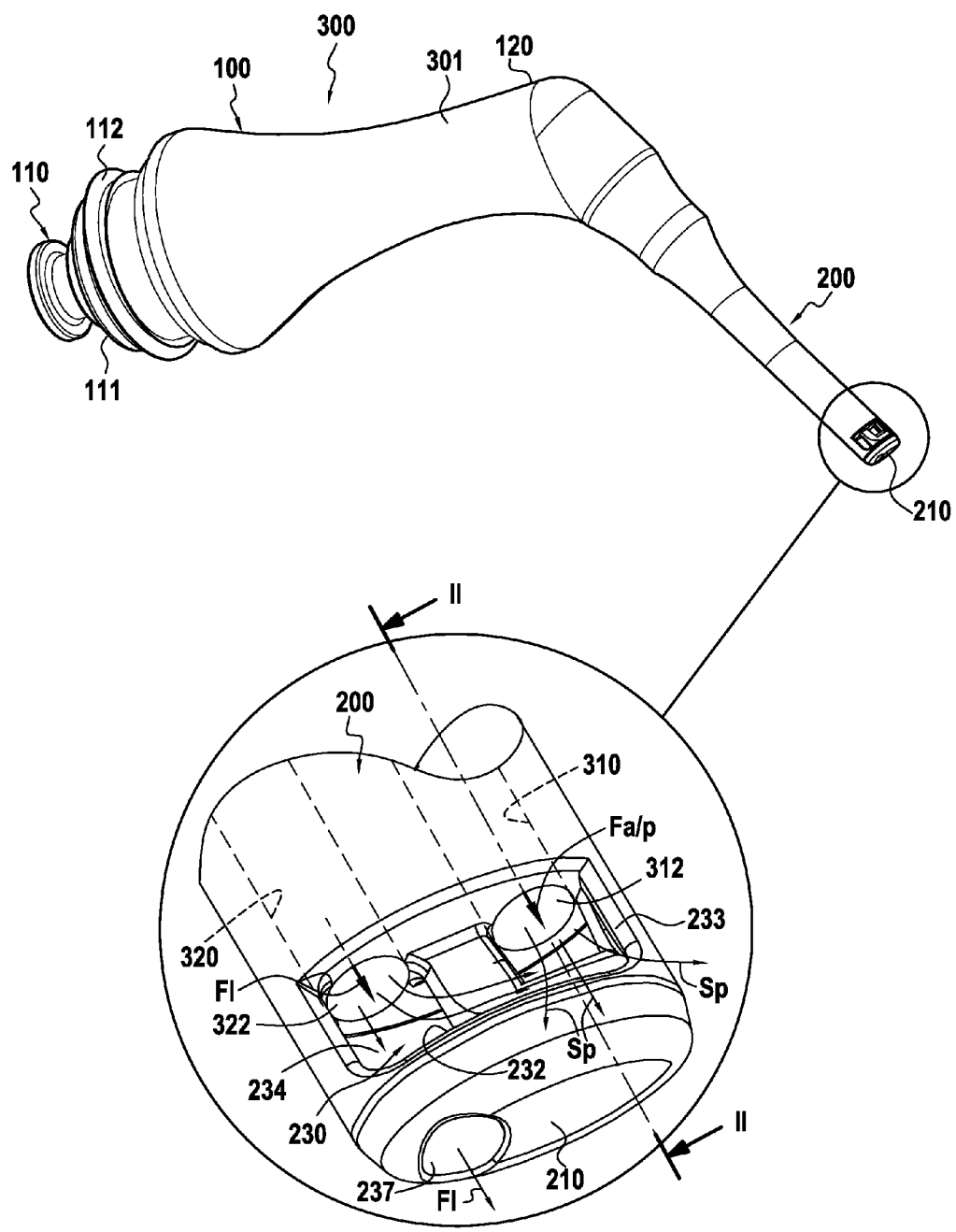
FIG. 1 is a perspective view and a detail view of a nozzle for a polisher in accordance with an embodiment of the invention.
Figure 4:
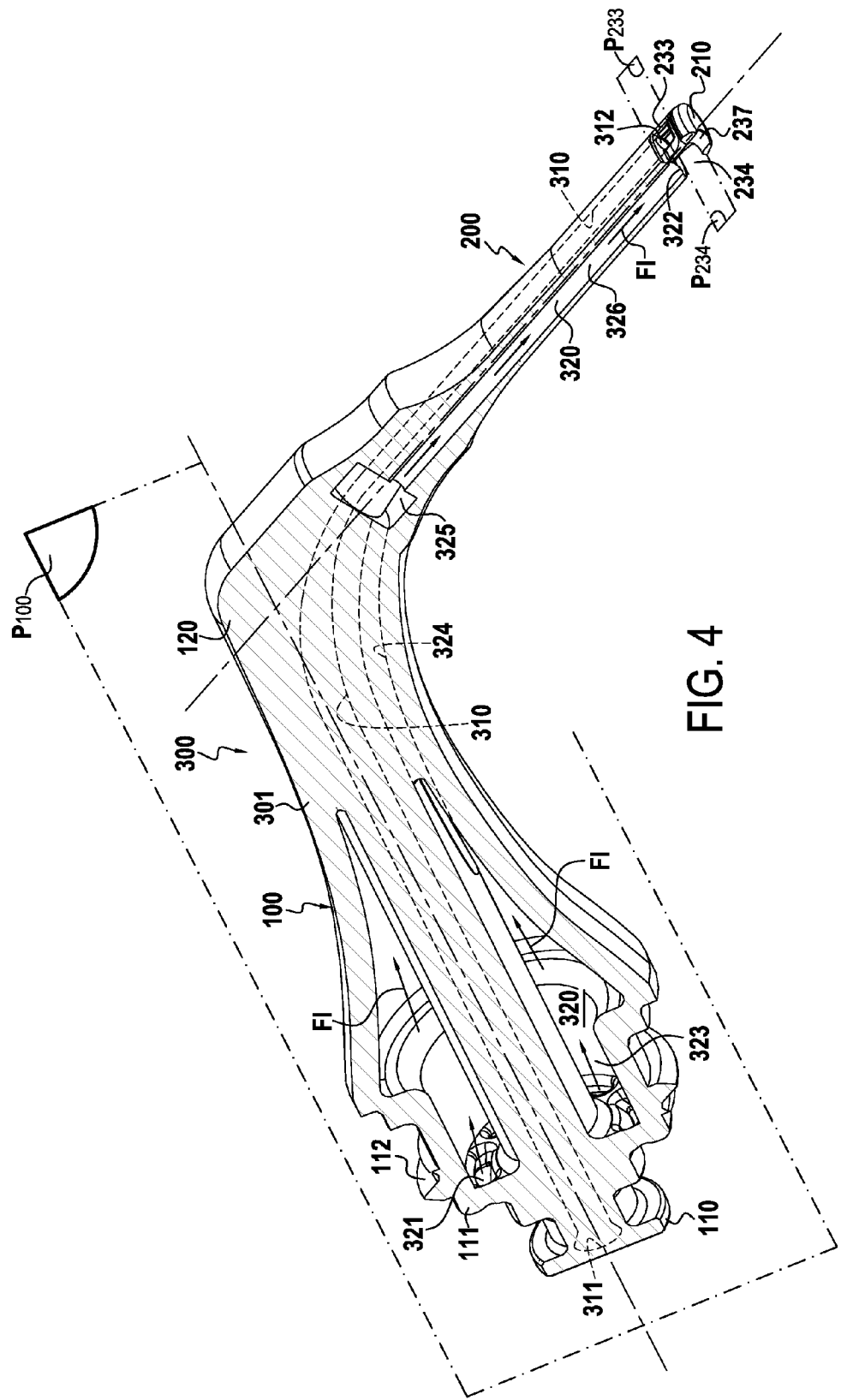

FIGS. 1, 3, and 4 show a nozzle 300 for delivering at least one spray constituted by a mixture of air and powder and a fluid such as water, for example.

The nozzle 300 is made up of a body 301 that extends between a proximal portion 100 for coupling mechanically with a handpiece for feeding an air/powder and fluid mixture as explained below, and a distal portion 200 with the air/powder and fluid mixture being delivered from the end thereof.

The proximal portion 100 has a free end 110 including a connector 111 fitted with a gasket 112 in order to enable a leaktight connection to be made between the handpiece and the nozzle 300. The opposite end 120 of the proximal portion 100 is extended by the distal portion 200 of the nozzle 300.

The nozzle 300 has a first internal channel 310 and a second internal channel 320, each extending inside the body 301 from the free end 110 of the proximal portion. More precisely, as shown in FIG. 3, the first internal channel 310 is provided at the center of the proximal and distal portions 100 and 200, and it opens out at the inlet of the nozzle 300 via an inlet orifice 311 and at the outlet of the nozzle via an outlet orifice 312, itself opening out into a chamber 230 formed in the distal portion 200 in the vicinity of its free end 210.

The second internal channel 320 opens out at the inlet to the nozzle 300 via an inlet orifice 321 and at the outlet from the nozzle via an outlet orifice 322, itself opening out into the chamber 230 (FIGS. 3 and 4). The second internal channel 320 presents an annular first portion 323 forming, from the free end 110 of the proximal portion 100, a duct that extends around the first portion 311 of the first internal duct 310 in the proximal portion 100. In the example described here, the first annular portion 323 initially presents a shape that is cylindrical and then a shape that is frustoconical. The end of this first portion (end of the portion having a frustoconical shape) co-operates with a second portion 324 of the internal channel 320 that extends along and parallel with the first internal duct 310 (FIG. 3). This second portion 324 opens out into a junction third portion 325 that surrounds the first internal duct 310 at least in part (FIGS. 3 and 4). This third portion connects the second portion 324 to the fourth portion 326 of the second internal duct that extends parallel to a second portion 312 of the first duct 310 situated in the distal portion 200 of the nozzle 300 and as far as the outlet orifice 322 of the second internal channel 320 (FIG. 4).

The first and second portions 323 and 324 of the second internal duct 320 are situated mainly in the proximal portion 100 of the nozzle 300, whereas the third and fourth portions 325 and 326 are situated in the distal portion 200 of the nozzle 300.

As shown in FIGS. 1 to 4, the free end 210 of the distal portion includes the chamber 230 into which the first and second internal channels 310 and 320 open out via the respective outlet orifices 312 and 322.

Figure 5:
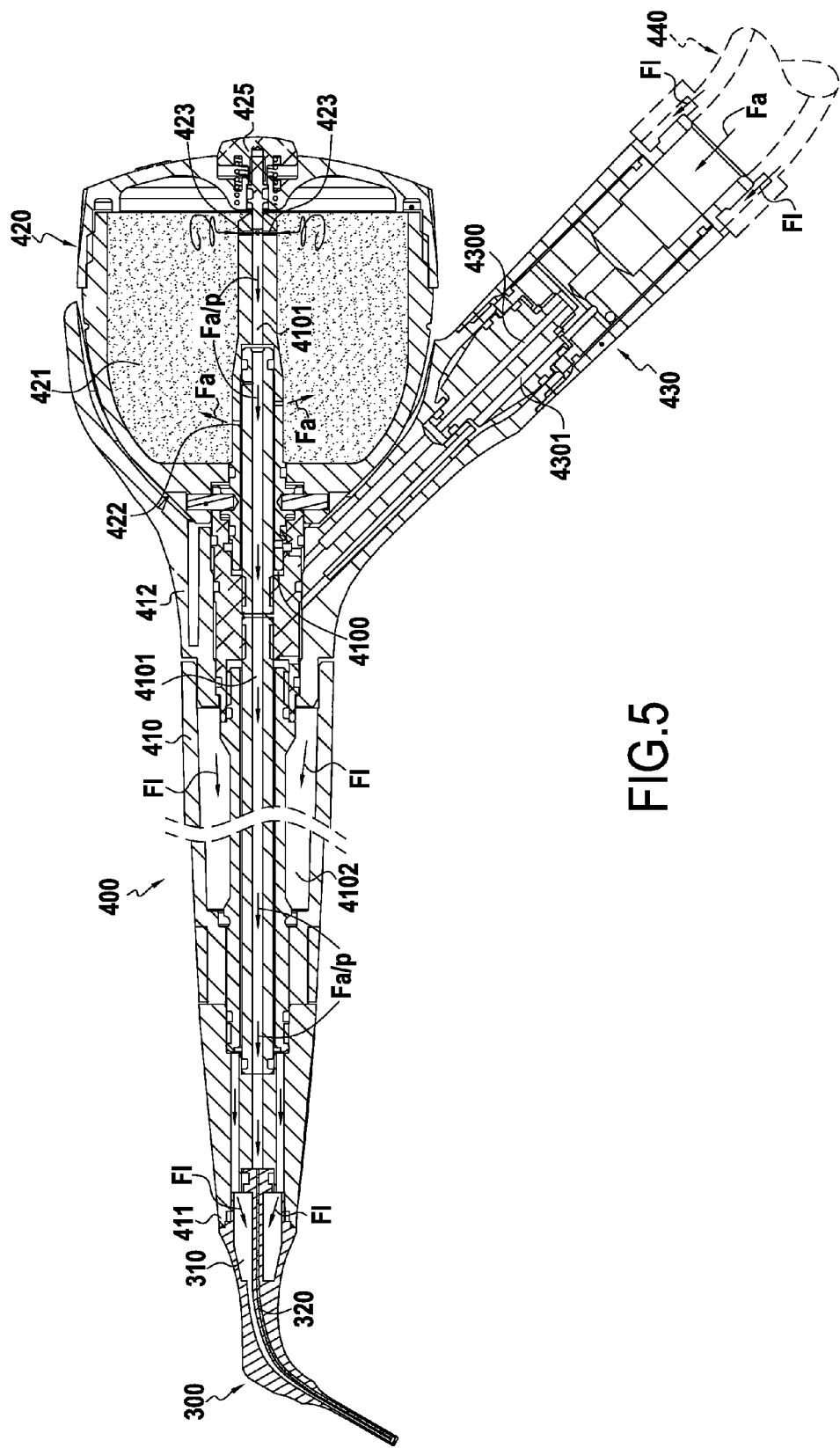
FIG. 5 is a section view of a polisher fitted with a nozzle of the invention.

In FIG. 5, the nozzle 300 is mounted on a handpiece 400. The handpiece 400 comprises a body 410 having its front end 411 connected to the nozzle 300 and its rear end 412 connected to an interchangeable tank 420 containing dental powder 421. The handpiece 400 also includes a coupling portion 430 for coupling to a connector 440 itself connected to a compressor (not shown) for delivering a stream of air $F_a$ under pressure into the handpiece, and to a pump (not shown) for sending a liquid flow $F_l$, such as water, into the handpiece.

The stream of air $F_a$ conveyed by the connector 440 enters into the handpiece 400 via a duct 4300 formed in the coupling portion 430 and is then taken to an inlet 422 of the tank 420 by a duct 4100 formed in the body 410 of the handpiece. Once it has entered into the tank 420, the fluid $F_a$ puts the powder 421 contained in the tank into suspension and entrains a fraction thereof towards a takeoff opening 423 of a duct 4101 that is present in the tank 420 and that extends in the body 410 of the handpiece 400 as far as its front end 411. An air/powder mixture $F_{a/p}$ is thus entrained into the duct 4101. The supply of powder to the duct 4101 may be stopped by acting on a piston 425 that serves to close the takeoff opening 423.

The liquid fluid $F_l$ conveyed by the connector 440 enters into the handpiece 400 via a duct 4301 formed in the coupling portion 430 and is then taken to the front end 411 of the body 410 of the handpiece via a duct 4102 formed in the body of the handpiece.

The duct 4102 co-operates at the front end 411 of the handpiece 400 with the first internal channel 310 of the nozzle 300 that is for delivering the liquid fluid $F_l$ to the chamber 230. In addition, the duct 4101 co-operates at the front end 411 of the handpiece with the second internal channel 320 of the nozzle that serves to deliver an air/powder mixture $F_{a/p}$ into the chamber.

In accordance with the present invention, the nozzle 300 has a chamber 230 arranged in the vicinity of the free end 210 of the distal portion 200 (detail view of FIG. 1). The chamber 230 is formed by an internal volume or recess formed close to the free end 210 of the distal portion 200 of the nozzle and that extends between the outlet orifices 312 and 322 of the internal channels 310 and 320 respectively and an end wall of the chamber 232. The chamber 230 also has two lateral openings 233 and 234 formed on the wall of the distal portion 200 and enabling a spray $S_p$ to be ejected out from the nozzle, the spray $S_p$ being constituted by the combination within the chamber of a portion of the liquid fluid $F_l$ and of the air/powder mixture $F_{a/p}$. The lateral openings 233 and 234 are arranged respectively on opposite sides of the distal portion. The nozzle of the present invention could equally well have only one of the two lateral openings 233 or 234.

Figure 6:
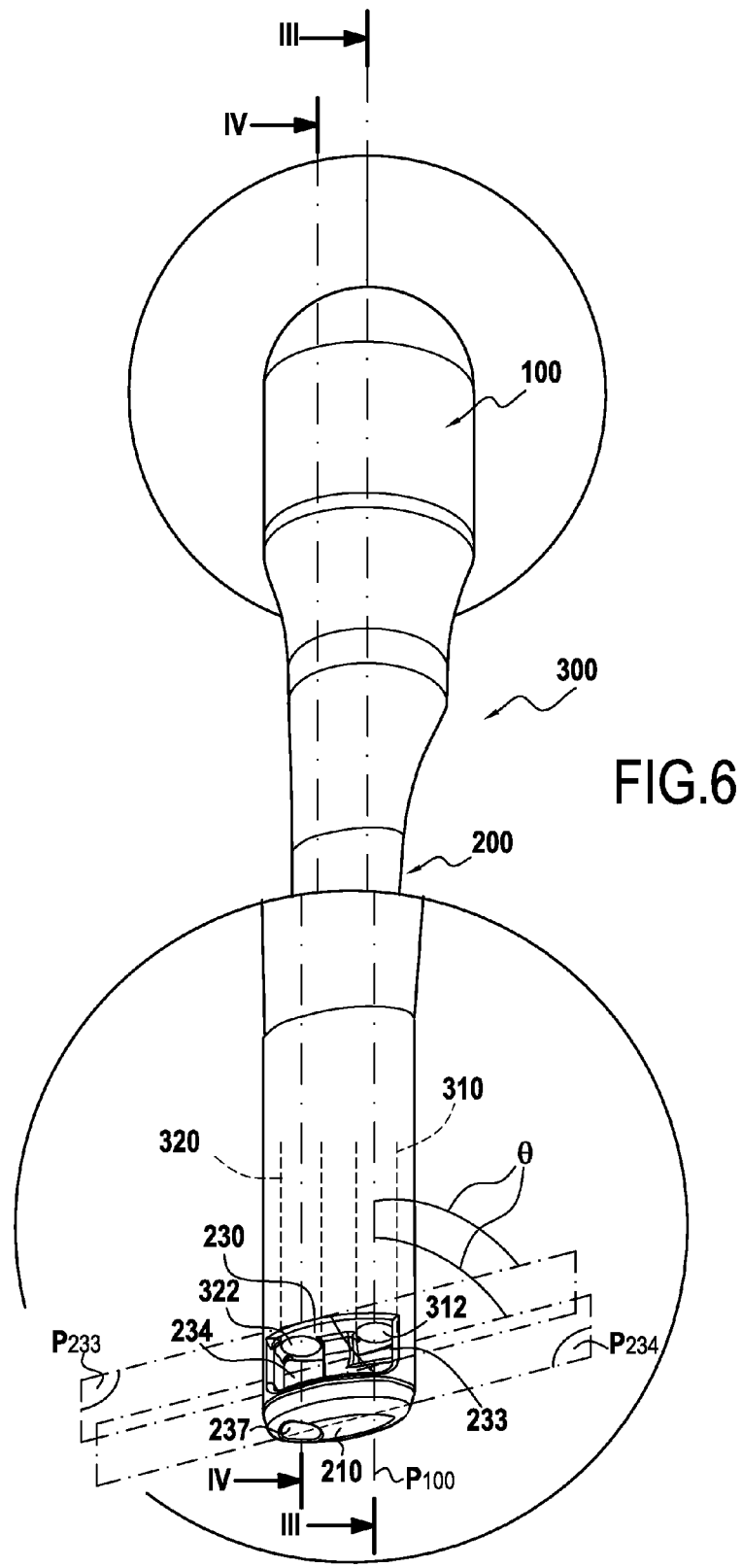
FIG. 6 is another perspective view and a detail view of the nozzle of FIG. 1.
Figure 7:
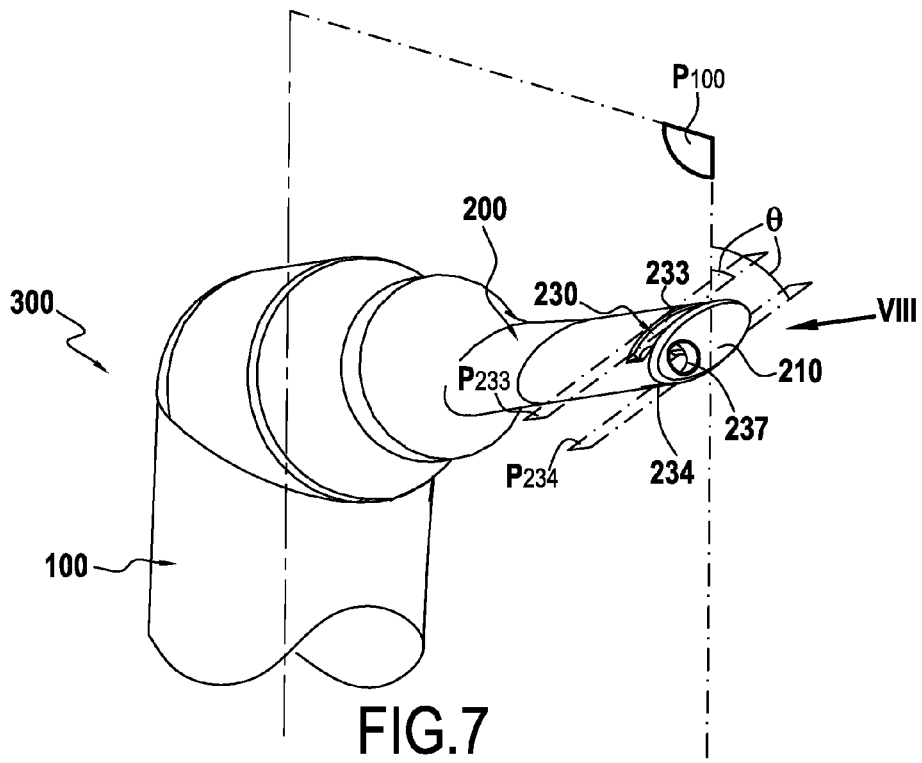
FIG. 7 is a fragmentary perspective view of the nozzle of FIG. 1.
Figure 8:
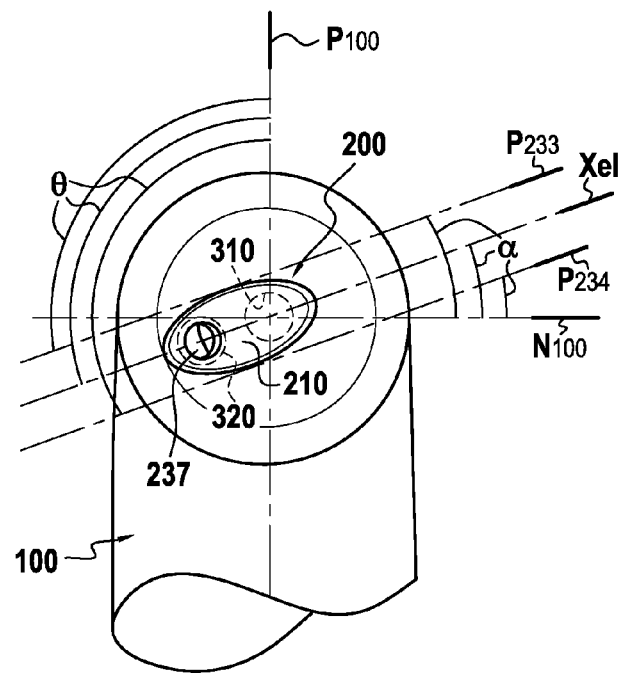
FIG. 8 is an end view of the FIG. 7 nozzle seen looking along arrow VIII.

In accordance with the invention, and as shown in FIGS. 6 to 8 in particular, the lateral openings 233 and 234 extend in parallel planes $P_{233}$ and $P_{234}$ that form an angle θ with the vertical axial plane $P_{100}$ of the proximal portion 100. Since the proximal portion 100 is in axial alignment with the body 410 of the handpiece 400, the vertical plane $P_{100}$ also corresponds to the vertical axial plane of the handpiece 400 and to the orientation in which the handpiece is held by the practitioner while using it (orientation of the handpiece shown in FIG. 5).

As shown in FIG. 6, the angle θ formed by the planes $P_{233}$ and $P_{234}$ of the lateral openings 233 and 234 relative to the vertical axial plane $P_{100}$ of the proximal portion 100 lies in the range 45° to 90°, the angle θ preferably being about 70°.

As shown in FIG. 7, the angle of the lateral openings 233 and 234 may also be defined relative to the normal $N_{100}$ to the vertical axial plane $P_{100}$ of the proximal portion 100. Under such circumstances, the planes $P_{233}$ and $P_{234}$ of the lateral openings 233 and 234 form an angle α relative to the normal $N_{100}$ that lies in the range 0° to 45°, with the angle α preferably being about 20°.

This angle of the lateral openings relative to the vertical axial plane of the proximal portion makes it easier to perform treatment in the vicinity of the molars without being hindered by the patient's cheeks. With prior art nozzles (angle θ of 180°), certain pockets cannot be treated.

According to a particular aspect of the invention as shown in particular in FIG. 2, the end wall 233 of the chamber 230 has two deflectors 235 and 236 facing the outlet orifice 312 of the first internal channel 310. The deflector 235 presents a slope 2350 that is inclined towards the lateral opening 233, while the deflector 236 presents a slope that is inclined towards the lateral opening 234. The deflectors 235 and 236 thus enable the air/powder mixture $F_{a/p}$ that is delivered by the outlet orifice 312 of the internal duct 310 to be directed towards the respective lateral openings 233 and 234. For a nozzle that has only one lateral opening, the chamber has only one deflector for directing the air/powder mixture $F_{a/p}$ towards the sole lateral opening. Under such circumstances, the tip of the deflector is preferably offset towards the side of the outlet orifice of the internal channel that is remote from the lateral opening so as to deflect all of the air/powder mixture $F_{a/p}$ towards the single lateral opening.

In another particular aspect of the invention, the end wall 232 of the chamber 230 presents an opening 237 that opens out to the free end 210 of the distal portion 200 (FIGS. 1, 6, and 7). The opening 237 is in alignment with the outlet orifice 322 of the second internal channel 320 so as to enable a fraction of the liquid fluid $F_l$ to be delivered directly to the end 210 of the distal portion 200 of the nozzle 300. In conjunction with actuating the piston 425 in order to stop the delivery of powder 421, the presence of the opening 237 makes it possible to obtain a small syringe effect.

According to yet another aspect of the invention, the distal portion 200 may, as in the example described herein, present an elliptical shape with its major axis $X_{el}$ in alignment with the planes $P_{233}$ and $P_{234}$ of the lateral openings, thereby consequently forming likewise angles θ with the vertical plane $P_{100}$ of the proximal portion 100 and α with the normal $N_{100}$ to the vertical axial plane $P_{100}$. The elliptical shape of the distal portion 200 and its angle similar to that of the lateral openings makes it possible simultaneously to facilitate inserting the end of the nozzle between the jaw and the tooth of the patient and also treatment of the periphery of the tooth. Other shapes for the distal portion may also be envisaged, such as a cylindrical shape, for example.

The invention claimed is:

1. A dental polisher nozzle comprising a body extending between a proximal portion connectable to a handpiece and a distal portion,
    at least a portion of said proximal portion being formed about an axial plane aligned with the handpiece,
    said body including a first channel arranged to deliver a dental polishing powder and a second channel arranged to deliver a fluid,
    said distal portion including a chamber disposed in an area of the free end of said distal portion, said first and second channels opening out into said chamber, and
    said chamber including at least one lateral opening, the lateral opening extending in a second plane, the second plane being offset from the axial plane of said proximal portion by an angle (θ), wherein
    the chamber is formed by an internal volume that extends between outlet orifices of the first and second channels opening into said chamber and an end wall of the chamber formed on a side of the internal volume opposite from the outlet orifices of the first and second channels, the chamber being configured such that the dental polishing powder of the first channel and the fluid of the second channel are mixed throughout the internal volume, and
    the at least one lateral opening extends in a lateral wall of the distal portion.

2. The nozzle according to claim 1, comprising two opposite lateral openings each extending in a respective plane forming said angle with the vertical axial plane including said proximal portion.

3. The nozzle according to claim 1, wherein the angle formed between the plane of said at least one lateral opening and the vertical axial plane including the proximal portion lies in the range of 45° to 90°.

4. The nozzle according to claim 3, wherein the angle formed between the plane of said at least one lateral opening and the vertical axial plane including the proximal portion is about 70°.

5. The nozzle according to claim 1, wherein an end wall of the chamber includes an opening that opens out to the free end of the distal portion, said opening being in alignment with an outlet orifice of the second channel in the chamber.

6. The nozzle according to any one of claims 1 to 5, wherein an end wall of the chamber includes at least one deflector facing an outlet orifice of the first channel in the chamber in such a manner so as to direct the dental polishing powder delivered by the outlet orifice of the first channel towards the or each lateral opening of the chamber.

7. The nozzle according to any one of claims 1 to 5, wherein the distal portion presents an elliptical shape with its major axis forming the angle relative to the vertical axial plane including said proximal portion, the plane of said at least one lateral opening of the chamber being substantially parallel to the major axis of the ellipse.

8. A dental polisher comprising a dental handpiece comprising a first channel arranged to feed a dental polishing powder and a second channel arranged to feed a fluid, and the dental polisher nozzle recited in claim 1, wherein
    the proximal portion of the nozzle is connected to the handpiece,
    said first channel arranged to feed the dental polishing powder co-operating with the first channel in the nozzle, and
    said second channel arranged to feed a fluid co-operating with the second channel in the nozzle.

9. The polisher according to claim 8, comprising an interchangeable tank containing the dental polishing powder.

10. The polisher according to claim 9, wherein the first channel arranged to feed powder includes a powder-taking opening in the tank and said tank includes a piston arranged to close said powder-taking opening.

* * * * *